US009550969B2

(12) United States Patent
Chotteau et al.

(10) Patent No.: US 9,550,969 B2
(45) Date of Patent: Jan. 24, 2017

(54) FLEXIBLE BAG FOR CULTIVATION OF CELLS

(75) Inventors: Veronique Chotteau, Nacka (SE); Rafael Diana, Westborough, MA (US); Christian Kaisermayer, Vienna (AT); Eva Lindskog, Uppsala (SE); Craig Robinson, Westborough, MA (US); Jimmie L. Rucker, Westborough, MA (US); Kieron D. Walsh, Westborough, MA (US)

(73) Assignee: GE Healthcare Bio-Sciences AB, Uppsala (SE)

( * ) Notice: Subject to any disclaimer, the term of this patent is extended or adjusted under 35 U.S.C. 154(b) by 0 days.

(21) Appl. No.: 14/005,916

(22) PCT Filed: Mar. 16, 2012

(86) PCT No.: PCT/SE2012/050292
§ 371 (c)(1),
(2), (4) Date: Sep. 18, 2013

(87) PCT Pub. No.: WO2012/128703
PCT Pub. Date: Sep. 27, 2012

(65) Prior Publication Data
US 2014/0011270 A1    Jan. 9, 2014

Related U.S. Application Data

(60) Provisional application No. 61/454,138, filed on Mar. 18, 2011.

(30) Foreign Application Priority Data

Apr. 15, 2011    (SE) ....................................... 1150328

(51) Int. Cl.
*C12M 1/00*    (2006.01)
*C12M 3/06*    (2006.01)
(Continued)

(52) U.S. Cl.
CPC ........... *C12M 23/14* (2013.01); *B01F 11/0017* (2013.01); *B01F 15/0085* (2013.01); *C12M 27/16* (2013.01); *C12M 27/20* (2013.01)

(58) Field of Classification Search
CPC ....... C12M 41/14; C12M 41/34; C12M 41/40; C05F 11/0017; C05F 11/0085; C05F 17/027
See application file for complete search history.

(56) References Cited

U.S. PATENT DOCUMENTS 3,334,870 A     8/1967   Kropp et al.
5,362,642 A *  11/1994   Kern ............................. 435/404
(Continued)

FOREIGN PATENT DOCUMENTS

FR    WO 2009116002 A1 *  9/2009 .......... B01F 3/04269
JP    2009-284860            12/2009
(Continued)

OTHER PUBLICATIONS

Chaussin et al., English language machine translation (original WIPO publication is attached to the machine translation).*

*Primary Examiner* — Michael Hobbs
*Assistant Examiner* — Liban Hassan
(74) *Attorney, Agent, or Firm* — Wood IP LLC

(57) ABSTRACT

An inflatable bioreactor bag for cell cultivation, which comprising a top and a bottom sheet of flexible material, joined together to form two end edges and two side edges, wherein one baffle or a plurality of baffles extend from the bottom sheet in a region where the shortest distance to any one of the two end edges is higher than about one fourth of the shortest distance between the two end edges.

14 Claims, 12 Drawing Sheets

(51) Int. Cl.
  *B01F 11/00* (2006.01)
  *B01F 15/00* (2006.01)

(56) References Cited

U.S. PATENT DOCUMENTS

| | | | |
|---|---|---|---|
| 5,941,635 A * | 8/1999 | Stewart | 366/165.5 |
| 6,071,005 A * | 6/2000 | Ekambaram | B01F 5/0068 366/165.1 |
| 6,190,913 B1 * | 2/2001 | Singh | B01F 11/0017 435/383 |
| 6,544,788 B2 * | 4/2003 | Singh | 435/383 |
| 7,629,167 B2 | 12/2009 | Hodge et al. | |
| 2005/0158851 A1 * | 7/2005 | Furey | 435/289.1 |
| 2005/0186669 A1 * | 8/2005 | Ho | C12M 27/16 435/287.1 |
| 2005/0272146 A1 | 12/2005 | Hodge et al. | |
| 2006/0246546 A1 * | 11/2006 | Jenkins | C12P 21/00 435/69.1 |
| 2007/0128081 A1 * | 6/2007 | Ellis et al. | 422/100 |
| 2007/0128718 A1 | 6/2007 | Courtois et al. | |
| 2008/0206862 A1 | 8/2008 | Asgari | |
| 2009/0219780 A1 * | 9/2009 | Castillo et al. | 366/132 |
| 2009/0311775 A1 | 12/2009 | Kocourek et al. | |
| 2010/0203624 A1 | 8/2010 | Singh | |
| 2011/0020922 A1 | 1/2011 | Wuenn et al. | |
| 2011/0038222 A1 * | 2/2011 | Ludwig | B01F 3/04269 366/102 |

FOREIGN PATENT DOCUMENTS

| | | |
|---|---|---|
| WO | WO 2008/040568 | 4/2008 |
| WO | WO 2009115241 A3 * | 11/2009 |

* cited by examiner

FLEXIBLE BAG FOR CULTIVATION OF CELLS

CROSS-REFERENCE TO RELATED APPLICATIONS

This application is a filing under 35 U.S.C. 371 of international application No. PCT/SE2012/050292, filed Mar. 16, 2012, published on Sep. 27, 2012 as WO 2012/128703, which claims priority to U.S. provisional patent application No. 61/454,138 filed Mar. 18, 2011 and to Swedish patent application No. 1150328-1 filed Apr. 15, 2011.

TECHNICAL FIELD OF THE INVENTION

The present invention relates to flexible bags for cultivation of cells and more particularly to inflatable flexible bags for cultivation under agitation by rocking. The invention also relates to methods of cultivating cells in flexible bags.

BACKGROUND OF THE INVENTION

The bio-processing industry has traditionally used stainless steel systems and piping in manufacturing processes for fermentation and cell culture. These devices are designed to be steam sterilized and reused. Cleaning and sterilization are however costly labour-intensive operations. Moreover, the installed cost of these traditional systems with the requisite piping and utilities is often prohibitive. Furthermore, these systems are typically designed for a specific process, and cannot be easily reconfigured for new applications. These limitations have led to adoption of a new approach over the last ten years—that of using plastic, single-use disposable bags and tubing, to replace the usual stainless steel tanks.

In particular bioreactors, traditionally made of stainless steel, have been replaced in many applications by disposable bags which are rocked to provide the necessary aeration and mixing necessary for cell culture. These single-use bags are typically provided sterile and eliminate the costly and time-consuming steps of cleaning and sterilization. The bags are designed to maintain a sterile environment during operation thereby minimizing the risk of contamination.

Commonly used bags are of the "pillow style," mainly because these can be manufactured at low cost by seaming together two flexible sheets of plastic. Three-dimensional bags have also been described, where further sheets may be used to create wall structures.

One of the successful disposable bioreactor systems uses a rocking table on to which a bioreactor bag is placed. The bioreactor bag is partially filled with liquid nutrient media and the desired cells. The table rocks the bag providing constant movement of the cells in the bag and also efficient gas exchange from the turbulent air-liquid surface. The bag, typically, has at least one gas supply tube for the introduction of air, carbon dioxide, nitrogen or oxygen, and at least one exhaust gas tube to allow for the removal of respired gases. Nutrients can be added through other tubes.

When cells are cultured at high densities, the aeration may not be sufficient to supply the cells. Bags with baffles along the edges to improve the mixing have been described in US 2010/0203624 and U.S. Pat. No. 7,195,394 but these are not sufficient to reach the cell densities desired today. Accordingly there is a need for improved aeration in rocking table bioreactors.

Traditionally, cell culture has been operated in a batch mode. In batch operation, the bioreactor is seeded with culture medium and a small amount of cells and the cells are grown to higher density without any further nutrient supply. The cells eventually die due to lack of nutrients or to build-up of toxic metabolites, and this will ultimately determine at which point harvest takes place. This method has several drawbacks—firstly, critical nutrients may become depleted leading to low final cell densities and consequently lower product yields; secondly, formation and quality of a potential recombinant protein product is often impaired due to the build-up of toxic metabolic by-products.

An alternative mode of operation is fed-batch. It involves culture initiation in a basal medium, and at a certain time point starting a supplementation, feed, of specific nutrients that otherwise may become limited. These nutrients can be added separately, or in groups, and they can be supplemented continuously or batch-wise. This strategy will counter-act early nutrient depletion and the implication is to prolong the culture time, increase the max cell density and thereby increase the potential for a high yield of e.g. a recombinant protein produced by the cells. However, a fed-batch strategy does not generally hinder the build-up of toxic metabolites, and this will result in conditions that are changing during the course of the culture. These changes may adversely affect the quality of the product, e.g. in terms of a less favourable glycosylation pattern.

It has long been recognized that perfusion culture offers better economics for certain processes. In this operation, cells are retained in the bioreactor, and toxic metabolic by-products are continuously removed. Feed, containing nutrients is continually added. This operation is capable of achieving high cell densities and more importantly, the cells can be maintained in a highly productive state for weeks—months. This achieves much higher yields and reduces the size of the bioreactor necessary. It is also a useful technique for cultivating primary or other slow growing cells. Perfusion operations have tremendous potential for growing the large number of cells needed for human cell and genetic therapy applications. A new perfusion process with a strategy to retain not only the cells in the bioreactor vessel, but also the product, has recently been described and this has gained a certain interest in the bioprocess community. In this process, a hollow fiber filter with a low cut-off pore size is used to separate high molecular particles such as cells and target proteins such as antibodies, from low molecular waste products. The high molecular particles remain in the retentate and thus in the reactor and the low molecular weight ones are continuously removed. This strategy results in not only high cell densities but also very high product concentrations in the reactor vessel.

Another recent development in perfusion cultivation is the alternating tangential flow (ATF) method described in U.S. Pat. No. 6,544,424.

Perfusion culture in inflatable bags has been described in US 2011/0020922 and U.S. Pat. No. 6,544,788, both of which discuss filters to be applied inside the bag for removal of filtrate through tubing. This arrangement puts severe constraints on the filter construction and there is a significant risk of filter clogging. Moreover, if the filter clogs then the whole culture has to be transferred to a new inflatable bag. Hence there is a need for improved constructions to be used in flexible bag perfusion culture.

SUMMARY OF THE INVENTION

One aspect of the invention is to provide an inflatable bioreactor bag suitable for high density cell culture. This is achieved with a bag as defined in claim 1. One advantage of this construction is that the baffles provide improved mixing and aeration which allows for prolonged culture at high viable cell densities.

A further aspect of the invention is to enable efficient cell cultivation in inflatable bags. This is achieved with a method as defined in claim 14.

Further suitable embodiments of the invention are described in the dependent claims.

DEFINITIONS

The term "perfusion", as used herein, means a mode of cell cultivation where the cell medium is continuously exchanged while the cells remain in a bioreactor vessel. The exchange of cell medium can e.g. be performed over a filter, which means that inhibiting or toxic low molecular waste products can be removed and nutrients can be continuously added. The filter can be a microfilter, in which case target proteins expressed by the cells can be recovered in the permeate. It can also be an ultrafilter, which allows expressed proteins to remain in the cell suspension, so that they can be recovered in a batch harvest operation.

The term "baffle" as used herein means a physical body placed in an inflatable bioreactor bag, which is capable of perturbing the flow of fluids inside the bag during rocking of the bag.

The term "port" as used herein means an opening in an inflatable bag, adapted for transport of material into or out of the bag or for mounting of transducers. Ports are often equipped with tube fittings.

DETAILED DESCRIPTION OF EMBODIMENTS

Figure 1:
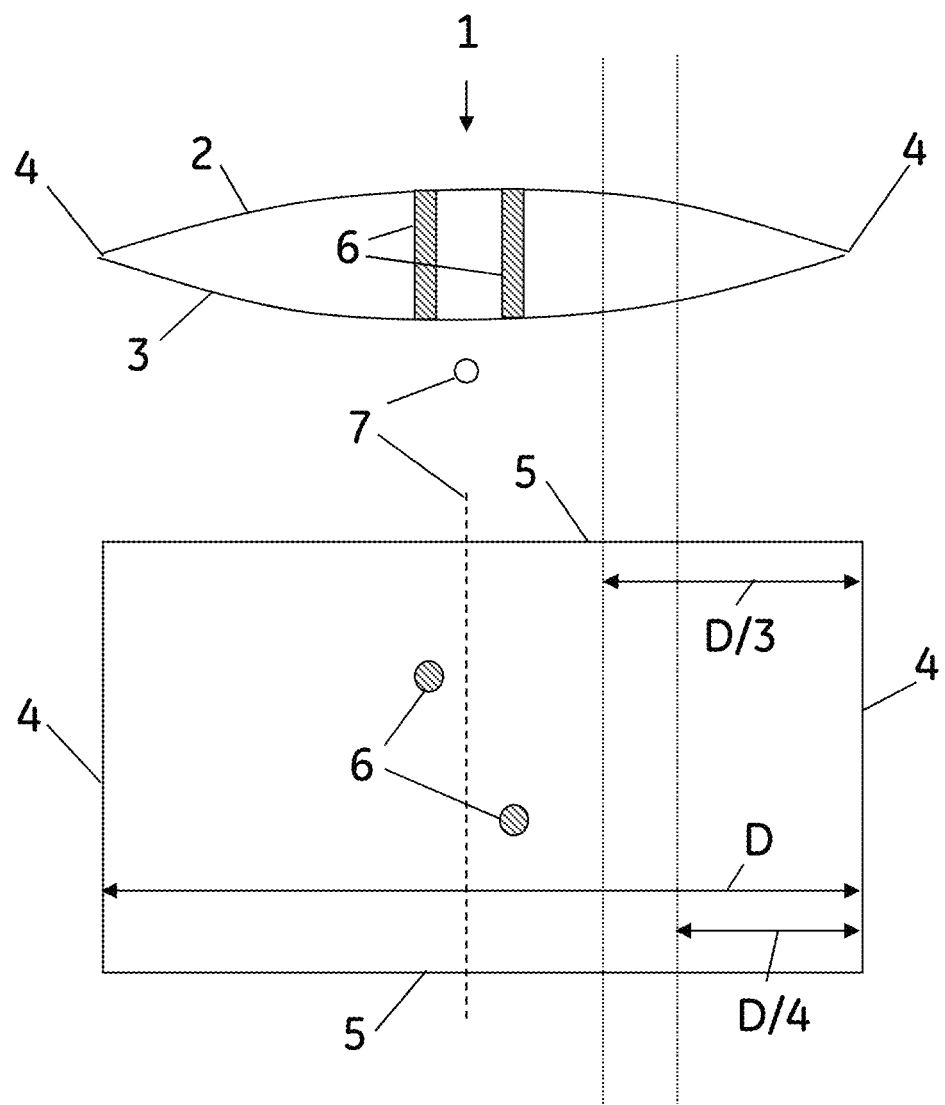
FIG. 1 shows (top and side view) an inflatable bioreactor bag with baffles according to the invention.
Figure 2:
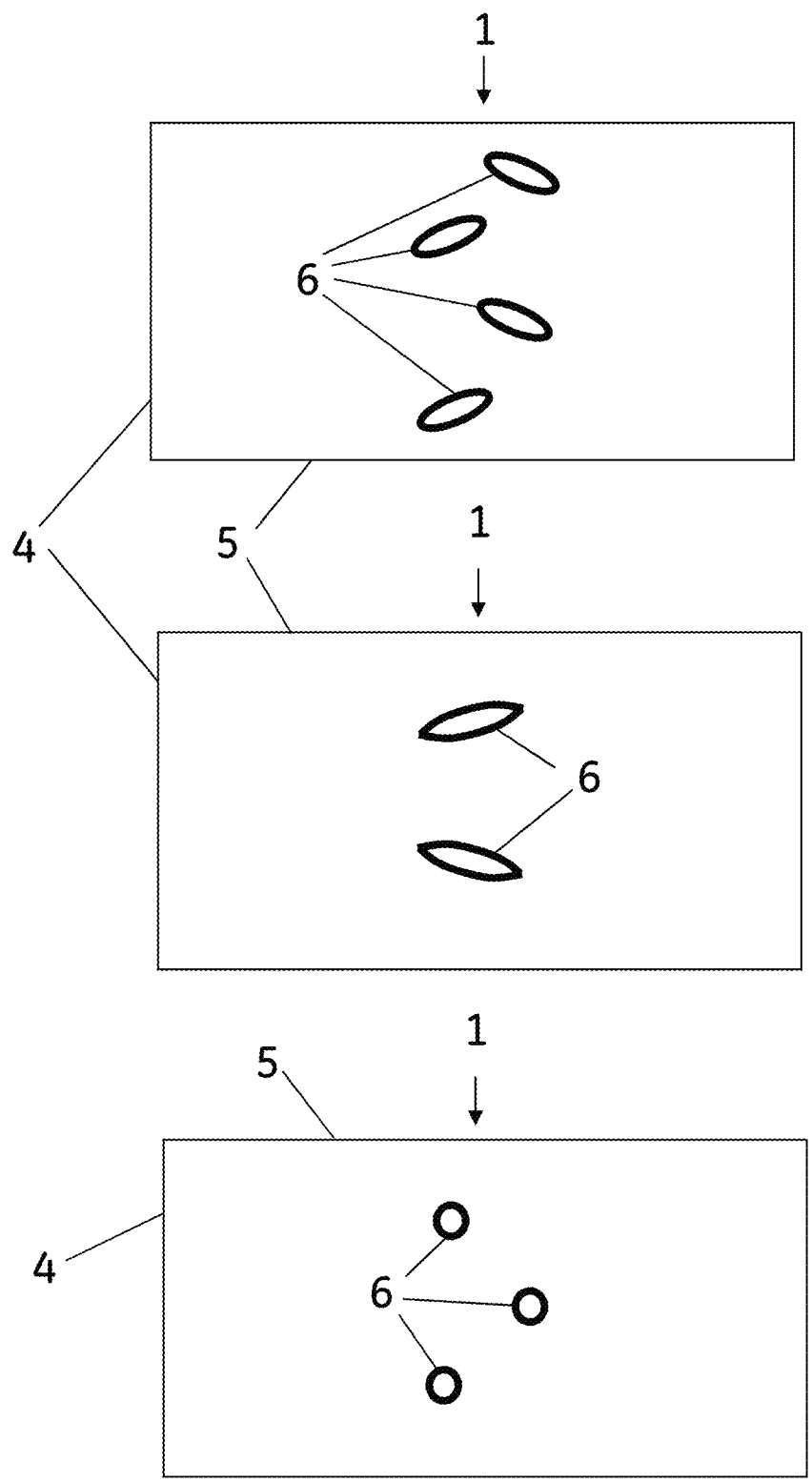
FIG. 2 shows (top views) bags with alternative baffle arrangements according to the invention.
Figure 3:
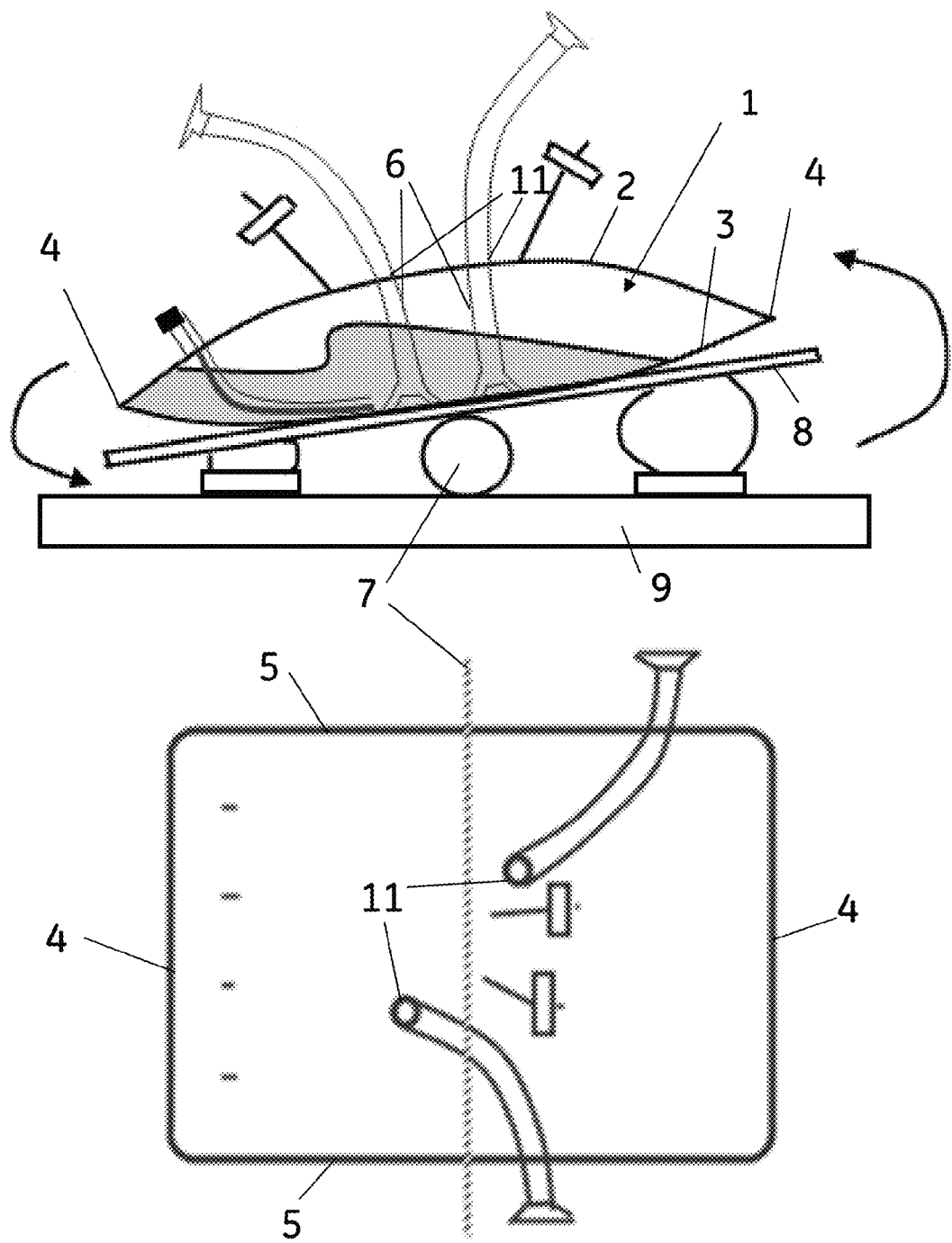
FIG. 3 shows (side and top view) a bag according to the invention, mounted on a pivotable support.
Figure 4:
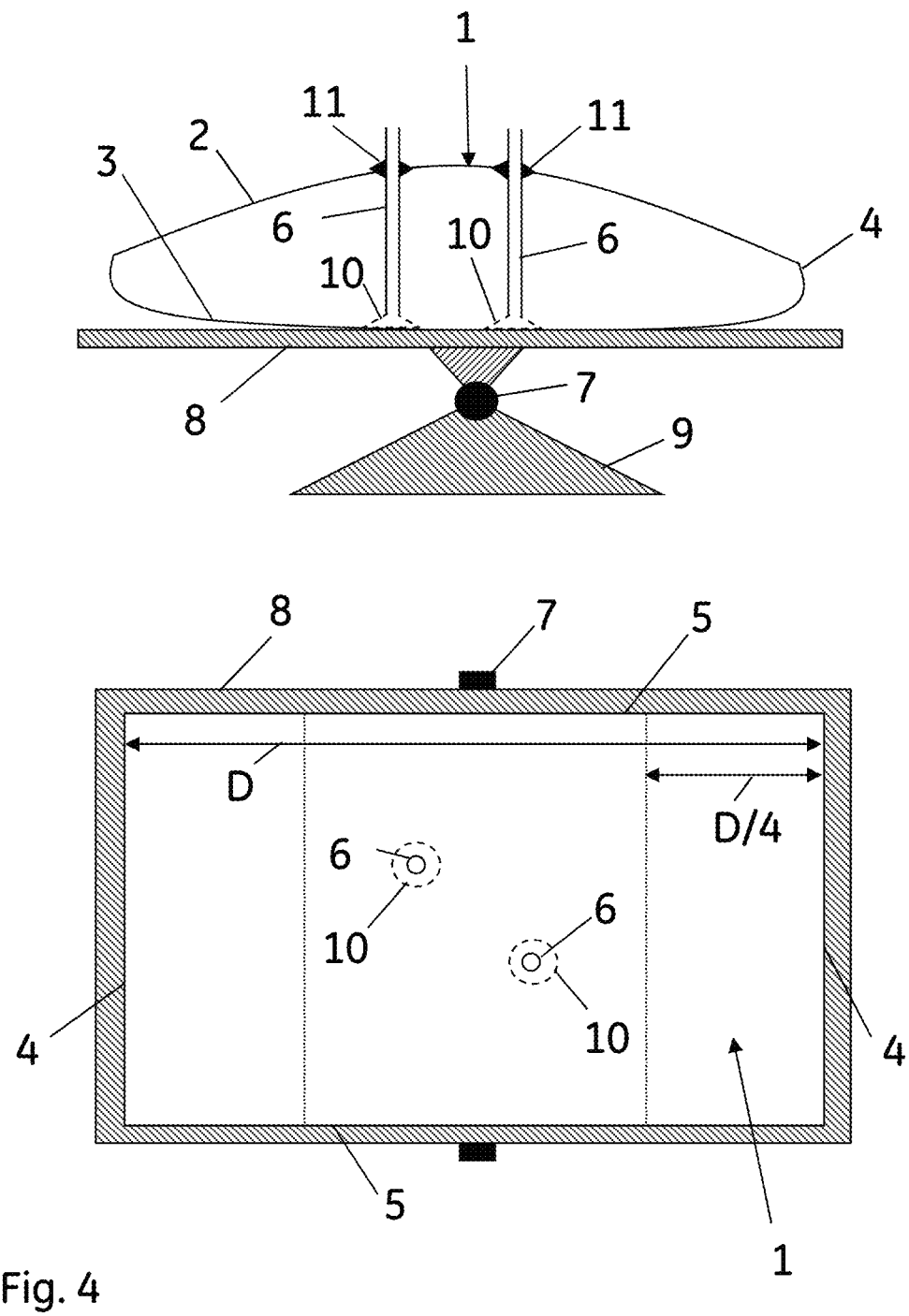
FIG. 4 shows (side and top view) a bag according to the invention, mounted on a pivotable support.

In one aspect illustrated by FIGS. 1-5, the present invention discloses an inflatable bioreactor bag 1 for cell cultivation, which bag comprises a top sheet 2 and a bottom sheet 3 of flexible material, joined together to form two end edges 4 and two side edges 5, wherein one baffle 6 or a plurality of baffles 6 extend from the bottom sheet 3 in a region of the bottom sheet 3 where the shortest distance to any one of the two end edges 4 (i.e. the closest end edge) is higher than about one fourth of the shortest distance D between the two end edges 4. The bag may be generally rectangular, in which case the shortest distance to any one (the closest one) of the end edges 4 will never be higher than D/2 for any point on the bottom sheet 3. Hence, the baffles 6 may extend from the bottom sheet 3 in a region where the shortest distance to the end edges 4 is between about one fourth and one half of the shortest distance D between the end edges 4, i.e. between D/4 and D/2. In some embodiments the distance to the end edges may be between D/3 and D/2. It can even be about D/2, so that the baffles 6 are located in the center of the bag. As illustrated in FIGS. 3 and 4, the bag 1 may be pivotally mounted to a base 9 about a movable axis 7 generally parallel to the end edges 4. The movable axis 7 may be located below the bag 1 and the bag may be mounted on a support 8, e.g. with the distance between each edge 4 to the projection of the movable axis 7 on the bottom sheet 3 being approximately equal to D/2. Suitable pivotable supports mounted on a movable axis can be e.g. the WAVE Bioreactor™ Systems (GE Healthcare). The flexible material of the top 2 and bottom 3 sheets may be a polymeric material, such as a plastic film or laminate with a thickness e.g. in the 50-500 micron range. A laminate may in addition to one or more polymeric materials comprise e.g. bather layers, which may be polymers or inorganic oxides or metals. The top sheet 2 in particular can be transparent to ensure visibility into the bag. The top sheet 2 and the bottom sheet 3 are defined with respect to the positions during use of the bag, i.e. in use the top sheet 2 is located above the bottom sheet 3. The top and bottom sheets may also be distinguished in that the ports 11;P1-P10;42;52 are preferably located on the top sheet 2, providing a smooth outer surface of the bottom sheet 3, suitable for resting on the support 8. The side edges 5 may be longer than the end edges 4.

An advantage of the central location of the baffles 6 is that when the bag is partially filled with a cell suspension, inflated and rocking around the axis 7, essentially all the cell suspension will repeatedly pass by the baffles. This increases the agitation intensity and improves the gas exchange in the air-liquid interface, while the agitation is still mild enough not to cause any damage to the delicate cells.

In some embodiments the baffles 6 are joined to both the bottom sheet 3 and the top sheet 2. One advantage of this is that the stability of the baffles 6 is improved.

In certain embodiments, illustrated by FIGS. 1-4, the baffles 6 are generally cylindrical, e.g. with circular or generally elliptic cross sections. The shape of the cross sections may be a circle, an ellipse, a pointed ellipse, a hydrofoil (airfoil) or elongated drop shape etc, but they can also be angular, e.g. parallelograms, polygons etc. An advantage of the generally cylindrical geometry is that a suitable increase in agitation intensity can be provided. Another advantage is that the baffles can easily be manufactured from e.g. extruded rods or tubing.

In some embodiments, illustrated by FIGS. 2-4, at least one of the baffles 6, such as two baffles, is/are tubular. One advantage of this is that the baffles can be made flexible enough to allow for easy packing and storage of the collapsed bags before use, but rigid enough to sustain the hydrodynamic forces during operation of the bag. A further advantage is that the tubular structure allows for transport of materials through the baffle into or out of the bag. Tubular baffles can e.g. be prepared from elastomeric materials that allow collapse of the structure during packing of the bag but are resilient enough to give complete recovery of the open tubular shape when the bag is filled and/or inflated. The elastomeric material can e.g. be a cross-linked silicone rubber or other vulcanised rubber material. If tubing with thick walls and/or high rigidity is used, the tubular baffles may also act as columns, keeping the top and bottom sheets of the bag separated before and during inflation of the bag.

Figure 5:
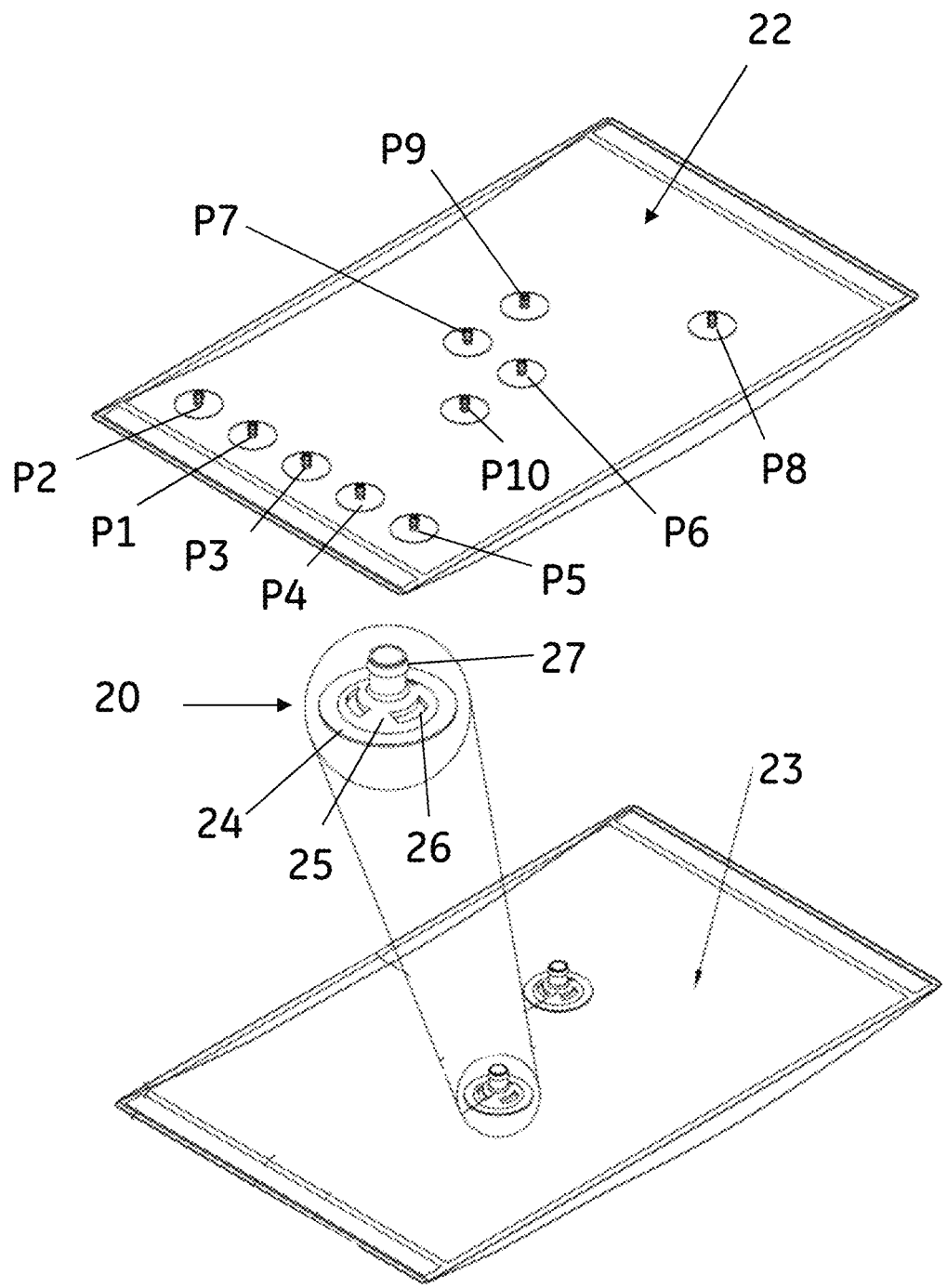
FIG. 5 shows the top sheet and bottom sheet of a bag according to the invention.
Figure 6:
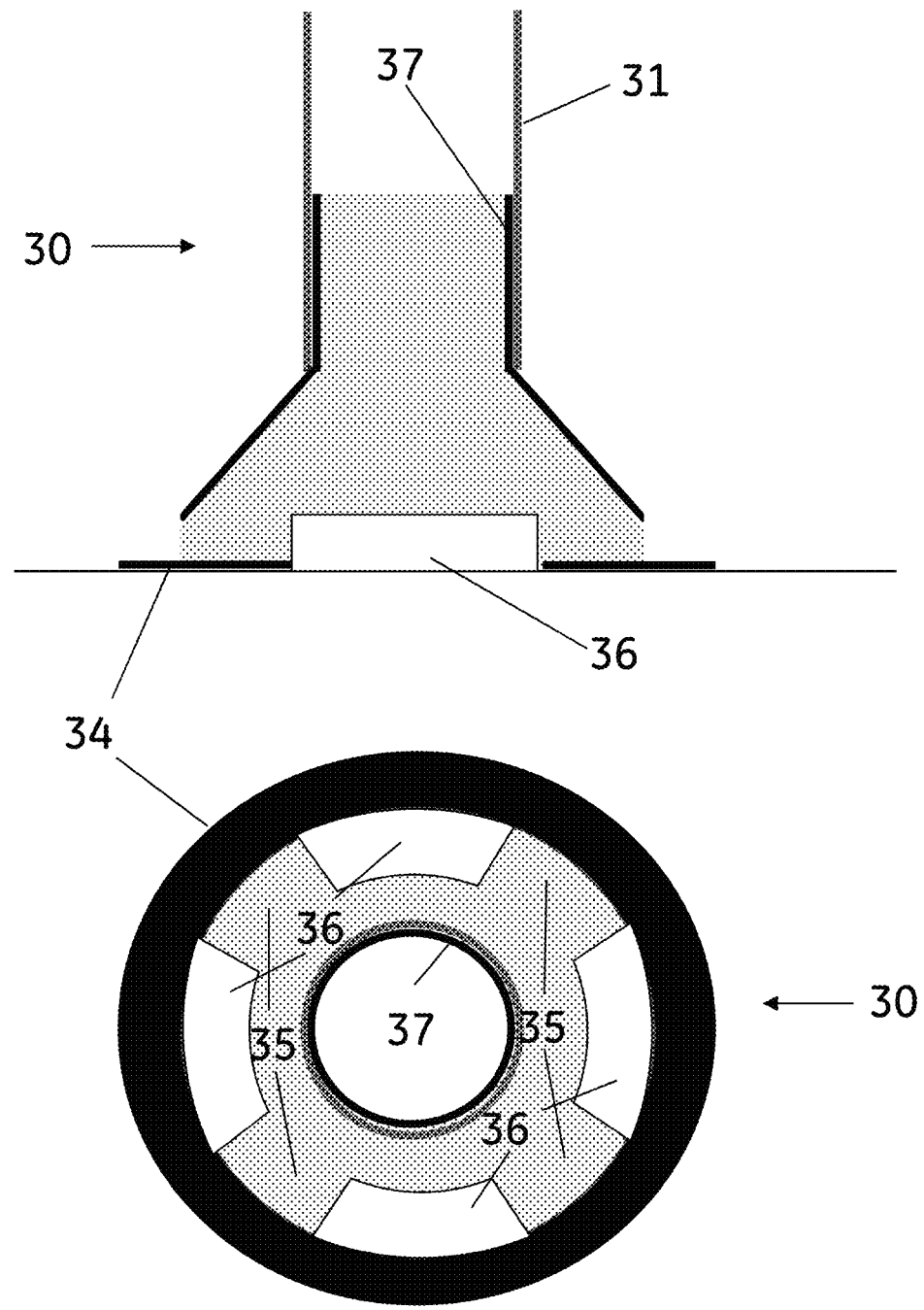
FIG. 6 shows a cell suspension diffuser according to the invention.

In certain embodiments, illustrated by FIGS. 4,5 and 6, the tubular baffle(s) 6;31 can be joined to the bottom sheet 3;23 via cell suspension diffusers 10;20;30, e.g. one cell suspension diffuser per baffle 6;31, and to the top sheet 2;22 via inlet/outlet ports 11;P9;P10, e.g. one inlet/outlet port per baffle. A cell suspension diffuser 10;20;30 can be a structure that allows for transport of cell suspension (typically cells suspended in growth medium) from the bag into the lumen of the tubular baffle or from the lumen into the bag. To accomplish this without risking clogging by cells, the cell suspension diffuser can have openings 26;36 which are several orders of magnitude larger than the cells, e.g. with no dimension smaller than about 1 or 2 mm. The cell suspension diffuser—tubular baffle assembly can be designed to provide an open flow-path for the cell suspension through the diffuser and baffle, without any impeding structures. The tubular baffles 6;31 may in these embodiments also be called dip tubes. The inlet/outlet port(s) 11;P9;P10 on the top sheet may comprise tube fittings on both the inside and outside to be able to attach tubular baffles (dip tubes) on the inside and tubing on the outside. They may on the outside also comprise sterile connectors, either integrated in the ports or attached via tubing. Examples of sterile connectors include e.g. ReadyMate™ connectors (GE Healthcare) which allow the connection of internally sterile flow-path components such as bags, tubing, sensors, pump heads, valves, filters (e.g. hollow fiber filters) etc., under normal ambient conditions to create a complete assembly with a sterile flow-path. Alternatively, the components may be connected by aseptic welding of thermoplastic tubing, using e.g. a Sterile Tube Fuser (GE Healthcare).

In some embodiments the bag is equipped with sterile connectors and irradiated. All the ports may be equipped with either closures, sterile connectors or sterile filtration-grade filters, so that microorganisms are not able to penetrate into the bag. The bag may then be irradiated with ionising radiation such as gamma radiation, electron beam or high-energy X-rays using a dose ensuring sterility depending on the bioburden of the bag assembly. The dose can e.g. be higher than 10 kGy, such as between 10 and 50 kGy. The bag, baffles, ports, connectors and filters can advantageously be constructed from radiation-resistant materials, e.g. ethylene (co)polymers, silicones, styrene (co)polymers, polysulfones etc.

In certain embodiments, at least one, such as each, baffle has a curved, such as generally sigmoidal shape. One advantage of this is that a sigmoidal baffle will intensify the agitation more efficiently in that the length of the baffle in contact with the cell suspension is longer compared to a straight baffle. Another advantage is that when tubular baffles (dip tubes) are connected to cell suspension diffusers and ports, the diffusers and ports can be located independently of each other, while still having the diffusers and ports perpendicular to the bottom and top sheets. Another advantage is that a sigmoidal baffle shape facilitates manufacturing, packaging and transport of the bag, as compared with a bag comprising a straight baffle. The shape may be curved in a plane generally parallel to the length axis of a baffle. The baffle(s) may be mounted such that this plane is generally parallel with the end edges 4 of the bag. With this mounting, the agitation will be particularly well intensified. Curved shape tubular baffles (dip tubes) can be manufactured e.g. by molding of elastomers such as crosslinked silicones.

Figure 7:
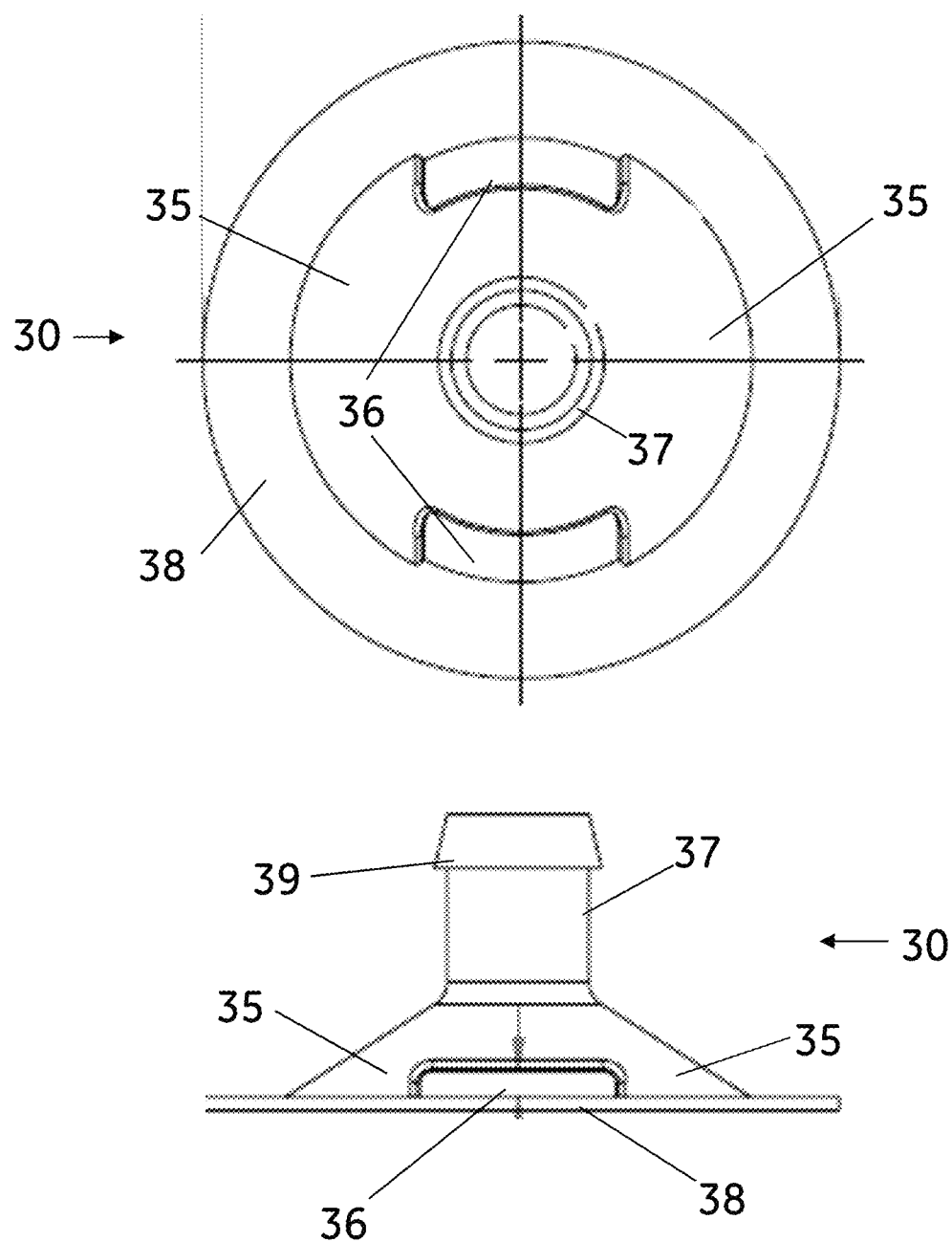
FIG. 7 shows a cell suspension diffuser according to the invention.

In some embodiments, illustrated by FIGS. 5-7, at least one, such as each, cell suspension diffuser 20;30 comprises a bottom ring 24;34 or plate 38, a plurality of struts 25;35 which join said bottom ring or plate to a tube connector 27;37 and a plurality of openings 26;36 between the struts. The number of openings can be e.g. two, three or four. The bottom ring 24;34 or plate 38 can be used to join the diffuser to the bottom sheet 3;23, e.g. by welding or by adhesive bonding, and can have an essentially planar side facing the bottom sheet 3;23. The struts 25;35 are load-bearing and should be dimensioned to be able to take up the loads caused by hydrodynamic forces during operation and the forces imposed during packaging and handling of the bag. As discussed above, the openings 26;36 can have both length and width larger than about 1 or 2 mm, such as length 5-25 mm and width 2.5-10 mm, depending on the size of the diffuser. The overall shape of the cell suspension diffuser 20;30 may be generally frustoconical with a cylindrical tube connector 27;37 on top of the frustocone. The tube connector 27;37 may comprise one or more barbs 39 to allow secure connection to a tubular baffle (dip tube)—the baffle/dip tube can in this case also be additionally secured with a tie such as a cable tie. Also the inside cavity of the diffuser 20;30 may be generally frustoconical to provide a smooth flow-path for the cell suspension. One advantage of the disclosed diffuser design is that is mechanically stable while allowing for an unimpeded cell suspension flow. A further advantage is that it is easily joined to the bottom sheet 3;23. Yet one advantage is that the openings 26;36 are close to the bottom sheet, which decreases the tendency for air bubbles to enter the tubular baffle (dip tube) during rocking of the bag, in particular when the diffusers are placed in vicinity of the projection of the pivoting axis 7 on the bottom sheet 3;23, such as in the region where the shortest distance to anyone of the two end edges 4 is higher than about one fourth or one third of the shortest distance D between the two end edges 4.

Figure 8:
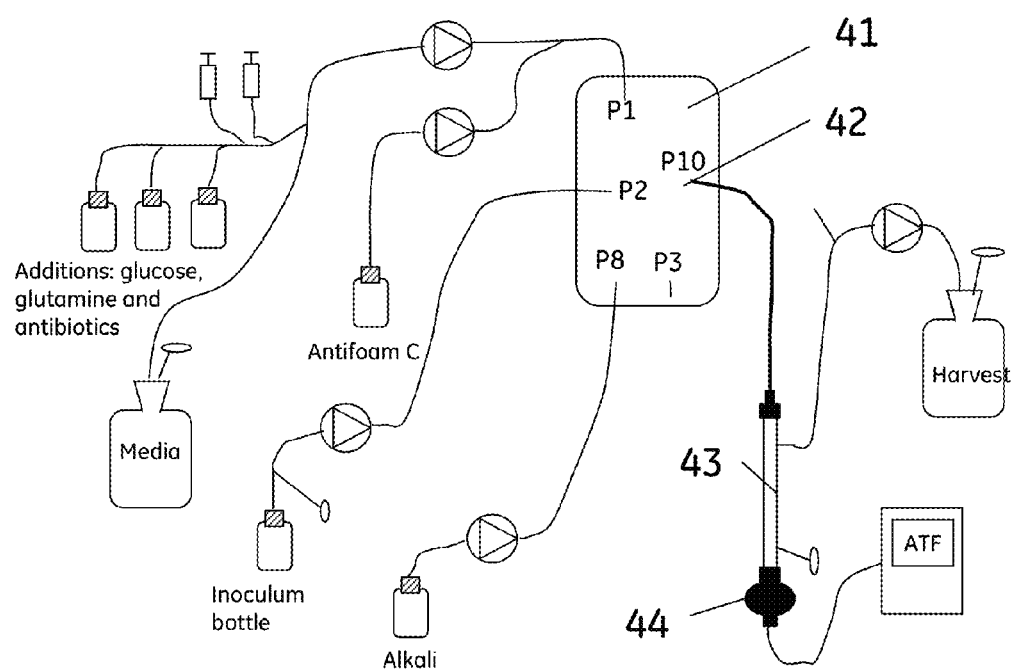
FIG. 8 shows a setup for ATF perfusion culture according to the invention.
Figure 9:
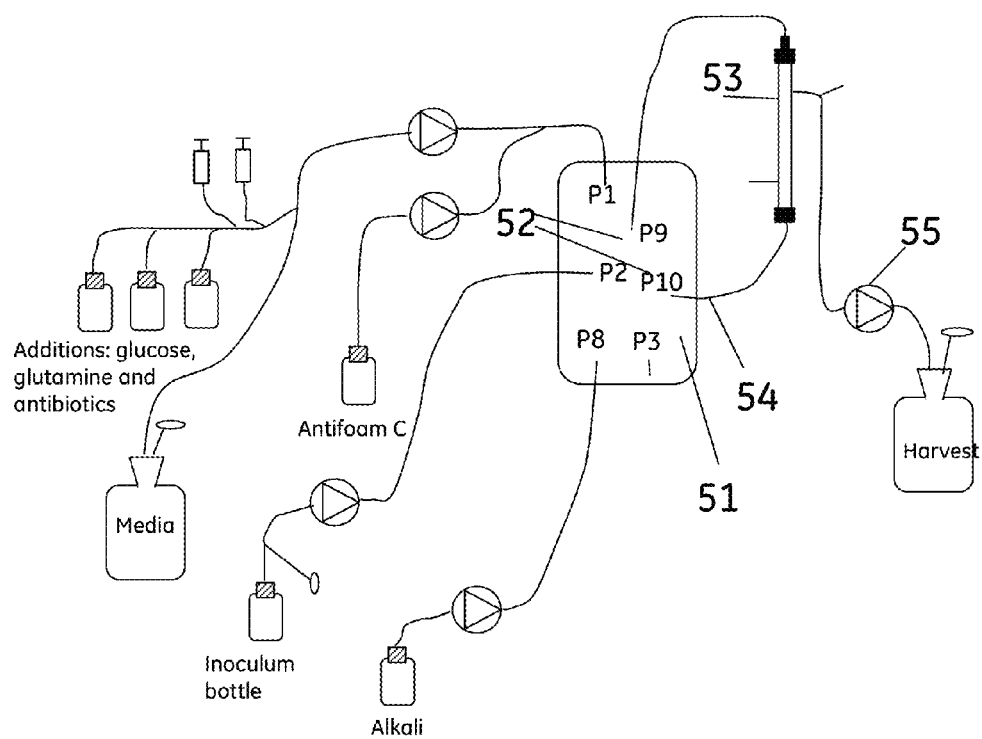
FIG. 9 shows a setup for TFF perfusion culture according to the invention.

In certain embodiments, illustrated by FIGS. 8 and 9, at least one of the ports 42;52 on the top sheet is further connected to a (or at least one) cell separating device, such as a (or at least one) at least one filter 43;53 and/or at least one gravitational device, outside the bag 41;51. The cell separating device may be any device capable of separating the cell suspension into a cell-rich fraction and a cell-depleted fraction. It can be a filter or e.g. a gravitational device such as a gravity settler, a centrifuge or a hydrocyclone. An advantage of connecting a cell separating device is that the bag can be used in perfusion cultivation of cells.

In some embodiments, illustrated by FIGS. 8 and 9, the filter 43;53 is a microfilter (typically with a pore size of 0.1-10 microns) or an ultrafilter (typically with a molecular weight cut-off of 1-1000 kDa) with a retentate side and a permeate side. Such filters can have many formats, e.g. hollow fiber cartridges, flat sheet cassettes, spiral modules, pleated filters, spin filters etc. A microfilter will retain the cells on the retentate side, while allowing all or almost all dissolved components of the suspension to pass over to the permeate side. This has the advantage that a target species such as a protein that is expressed by the cells can be continuously recovered from the permeate. An ultrafilter will retain the cells and the molecular weight cut-off can be selected so that a macromolecular target species is also retained in the retentate, while any small molecule toxic or cell-inhibiting metabolites pass over to the permeate and can be removed continuously. An advantage of this is that an efficient cell cultivation can be obtained and the target species can be recovered afterwards in one well-defined batch.

In certain embodiments, illustrated by FIG. 8, the cell separating device is further connected to a reciprocating pump 44, such as an air actuated membrane pump (available from e.g. Refine Technology, USA). Such a setup can be used in a perfusion cultivation method denoted ATF (alternating tangential flow), where the pump in the outward stroke draws the cell suspension past the cell separating device, e.g. a filter 43 such as a hollow fiber cartridge, and into the pump chamber. A cell-depleted fraction, e.g. a permeate is then created and on the inward stroke of the pump the cell suspension is again passing the cell separating device, prior to delivering the cell-enriched suspension back to the bag 41 through the tubular baffle (dip tube) and cell suspension diffuser.

In some embodiments, illustrated by FIG. 9, two of the ports 52 on the top sheet are connected via a pump 54 to the retentate side of the cell separating device, forming a retentate loop. In this case, cell suspension is drawn via one cell suspension diffuser and one tubular baffle (dip tube) via a first port through the retentate side of cell separating device and back to the bag 51 via a second port on the top sheet. The second port may be attached to a tubular baffle (dip tube) and a cell suspension diffuser, but it may also be attached just to a piece of tubing on the bag inside, as the return delivery of the cell suspension does not necessarily require a diffuser.

These embodiments are suitable e.g. for perfusion cultivation by tangential flow filtration (TFF). In this case, the cell separating device is a filter 53, such as a hollow fiber cartridge, a flat sheet cassette or a spiral module, and when the cell suspension passes through the retentate side of the filter, a cell-depleted fraction can be recovered as the permeate. A second pump 55 may be used to withdraw permeate from the filter In one aspect, illustrated by FIGS. 3, 4 and 10, the invention discloses a method for cell cultivation comprising the steps of a) providing an inflatable bioreactor bag 1 comprised of a top 2 and a bottom 3 sheet of flexible material, joined together to form two end edges 4 and two side edges 5, wherein one baffle 6 or a plurality of baffles 6 extend from said bottom sheet in a region where the shortest distance to any one (the closest one) of said two end edges 4 is higher than about one fourth of the distance between said two end edges 4, b) mounting said bioreactor bag on a support 8 pivotally mounted to a base 9 about a movable axis 7 generally parallel to said end edges 4, c) providing cell culture media and a cell inoculate to said bag 1, d) cultivating cells in the bag 1 with agitation provided by rocking said support 8 around said movable axis 7, forming a cell suspension and supplying at least one gas via a port in said top sheet 2.

An advantage of this method is that the presence of the centrally placed baffles provides efficient gas transfer to and from the cell suspension, giving good cell culture conditions and possibilities to reach high viable cell densities. The method may be carried out using any of the bag embodiments described above.

In certain embodiments, the cells during cultivation express a target biomolecule, such as a protein. The target biomolecule can be a protein, e.g. a monoclonal antibody, but it can also be a nucleic acid, e.g. a plasmid, or virus particles, e.g. for use as a vaccine or in gene therapy. The cells can be mammalian cells, e.g. CHO or MDCK cells, but they can also be e.g. insect cells, bacterial cells, e.g. E Coli or fungal cells, e.g. P Pastoris. The cells can be grown freely in suspension, but also on supporting particles such as microcarriers, e.g. Cytodex™ (GE Healthcare).

In some embodiments, illustrated by FIGS. 4-9, at least one baffle 6;31 is tubular and joined to said bottom sheet 3;23 via a cell suspension diffuser 10;20;30 and to said top sheet 2;22 via an inlet/outlet port 11;P9,P10, said method further comprising a step b') of connecting the inlet/outlet port 42;52 on said top sheet to at least one cell separating device, such as a filter 43;53, and a pump 44;54, and in step d) circulating said cell suspension over said cell separating device or filter via said cell suspension diffuser and tubular baffle. An advantage is that it is possible to carry out efficient perfusion cultivation with an external cell separating device. It is also possible to use this method whenever it is desired to manipulate the cell density during cultivation, e.g. for biomass reduction during culture or for volume reduction in connection with viral infection of host cells. The tubular baffles may in these embodiments also be called dip tubes.

In certain embodiments the filter 43;53 is a microfilter and the target biomolecule in step d) is recovered as a permeate, while a cell-rich retentate is recirculated to the bag 41;51. An advantage is that a continuous recovery of the target biomolecule can be achieved.

In some embodiments the filter 43;53 is an ultrafilter and in step d) the target biomolecule remains in a cell-rich retentate, which is recirculated to the bag 41;51. An advantage is that the target biomolecule can be recovered in a well-defined batch.

In certain embodiments the cell suspension is in step d) pumped over a retentate side of the filter 43 by an outward stroke of a reciprocating pump 44 and then pumped back by an inward stroke of said reciprocating pump over the retentate side into the bag 41 via the cell suspension diffuser. The reciprocating pump 44 may be an air-actuated membrane pump and it may be mounted directly on the filter, which may be a hollow fiber cartridge.

In some embodiments the cell suspension is in step e) pumped over a retentate side of the filter 53 in a loop back to the bag 51 via a port 52 on the top sheet, such as via a second tubular baffle (dip tube) and a second cell suspension diffuser. The pump 54 may be e.g. a peristaltic pump, a membrane pump or a centrifugal pump and it is also possible to add a second pump 55 to withdraw permeate from the filter 53.

In certain embodiments the density of viable cells is at least 40 or at least 150 MVC/mL, (million viable cells/mL) such as between 40 and 210 MVC/mL or between 100 and 210 MVC/mL. Using the method of the invention it is possible to conduct the cell cultivation at surprisingly high densities of viable cells.

In some embodiments the volume of the bag is at least 200 mL, such as between 200 mL and 500 L. The volume of cell suspension in the bag may be at least 40% of the bag volume, such as between 40 and 50%. An advantage of this is that the entrainment of air in the cell suspension diffusers is further diminished if the suspension volume is relatively high. The rocking rate can e.g. be 20-30 rockings per minute (rpm) and the rocking angle can be e.g. 6-8 degrees.

In certain embodiments the cultivation is performed in batch or fed-batch mode and at the end of the culture period, the cell suspension is withdrawn from the bag via a cell suspension diffuser, a tubular baffle (dip tube) and an outlet port and further via cell separating device, e.g. a filter, so that a cell-depleted fraction, filtrate or permeate comprising a target biomolecule can be recovered. The filter can be either a cross-flow/tangential flow filter, e.g. a hollow fiber cartridge, flat sheet cassette or spiral module or a normal flow filter, e.g. a pleated filter or depth filter. An advantage of using the disclosed bags in this way with a crossflow filter is that the bag itself can be used as a reservoir for the retentate loop of the filter and no transfer to any other vessel is needed. Due to the withdrawal of the cell suspension from the bottom of the bag, it is also easy to remove all the cell suspension from the bag, which is particularly important during normal flow filtration recovery of target biomolecules from large bags, which are very difficult to handle when filled with suspension.

EXAMPLES

Cell Line

A DHFR-CHO cell line producing IgG was used for all the experiments. During expansion cultures in shake flakes, methotrexate selection pressure was performed.

Cell Culture Medium and Additives

The cells were grown in IS CHO-CD XP medium (Irvine Scientific) supplemented with 4-5 mM glutamine. This medium contained 45 mM of Glucose for the first part of the first culture using TFF system. For the last part of this culture and the second culture using TFF system and for the cultures using ATF system, the initial concentration of glucose was lower than previously and close to 20-25 mM. In addition, for the latter cultivations, 3% of IS CHO Feed-CD XP supplement (Irvine Scientific, ref. 91122) was added in the medium. Hyclone medium PF-CHO Liquid Soy (Hyclone, ref. SH30359.02) supplemented with 3% of feed supplement (Sigma-Aldrich, ref. C1615) was also used. Initial concentrations of the major carbon and energy sources, i.e. glucose and glutamine were around 20-25 mM and 4 mM respectively. The culture medium was further supplemented with an antibiotic solution containing two antibiotics (Streptomycin and Penicillin G) and one antimycotic (Amphotericin) (Sigma-Aldrich). IS medium was provided as a powder and a reconstitution of the medium was required. The pH and osmolality were respectively adjusted to 7 (±0.1) and to 300-330 mM. Then, the medium was filtrated on 0.2 μm membrane (ULTA-XX, GE Healthcare). Medical Anti-foam C (Dow Corning, cat. 1811070-0705) was added up to 50 ppm concentration in the reactor by boost addition according to the apparition of bubbles in the tubular baffle/dip tube. Batch supplementations of glucose (Sigma-Aldrich, cat. G6152) or glutamine (Irvine Scientific, cat. 96700) were performed according to the cell need.

Cell Culture

Prior to seeding the Bioreactor, the cells were grown (for at least 4 passages) in shake flasks using IS medium. For all experiments, except mentioned in the text, CHO cells were inoculated with a seeding density of 0.5 MVC/mL (million viable cells/mL). The WAVE Bioreactor™ System 20/50, equipped with prototype 10 L WAVE Bioreactor Cellbags (top 22 and bottom 23 sheets 33×56 cm as shown in FIG. 5, with 7.5 cm sigmoidal silicone thermoformed rubber tubing connecting the P9 and P10 ports with the respective cell suspension diffusers 20, each having two 5×20 mm openings, on the bottom sheet 23) were used for all the cultivations. Table 1 describes the use of the different ports in and out of the bag in FIG. 5.

TABLE 1

In and Out ports of the FIG. 5 bag

| | |
|---|---|
| P4 | Dissolved oxygen (DO) probe |
| P5 | pH probe |
| P6 | Gas inlet with filter |
| P7 | Gas outlet with heater on filter |
| P3 | Septum for addition of syringe and sampling port |
| P1 | Addition pipe for medium and additives (Glc, Gln, anti-foam) |
| P10 | Tubular baffle/dip tube for cell suspension OUT (to ATF and TFF) and IN (TFF) |
| P8 | Tube for addition of alkali |
| P2 | Inoculation tube |
| P9 | Tubular baffle/dip tube for cell suspension IN (from TFF) |

The pH was controlled upwards by addition of 0.5 M Na2CO3 (dropping above liquid surface) and downwards by CO2 pulses in headspace (0-5% in air mix in head space). The dissolved oxygen (DO) was controlled upwards by pulses of O2 (0-100%) and/or by increase of rocking speed and downwards by decrease of rocking speed. The weight of the bioreactor was controlled during the perfusion by setting a set point weight (4 kg) and minimum and maximum deviation (±0.3 kg) from this set point. The set points of the cultures are indicated in Table 2.

TABLE 2

Set points (SP) used during the perfusion cultures

| Parameter | Set point/value |
|---|---|
| DO SP (%) | 30 or 35 |
| pH SP | 7.0 |
| Rocking rate (rpm) and angle (degrees) | 20-28 rpm and 5°-8° |
| Temperature SP (° C.) | 37.0 |
| Air flow in headspace (L/min) | 0.1-0.6 |
| Inoculation viable cell density (MVC/mL) | 0.5 |
| Working volume (L) | 4 |
| Perfusion rate (RV/day) | 1 or higher |
| Glucose concentration target during culture (mM) | >3.9 (>0.7 g/L) and <45 (<8 g/L) |
| Glutamine concentration target during culture (mM) | >0.05 (and <5) |
| Alkali | 0.5M $Na_2CO_3$ |
| Dilution of inoculate cell broth from seed container to production bioreactor larger than | 3 |

ATF Setup

The WAVE bioreactor was aseptically connected to a hollow fibre cartridge coupled to an ATF-2 pump (Refine Technology, USA), through the tubular baffle/dip tube (P10 port) on the bag (FIGS. 5 and 8). The exterior tube (c-flex, 8 mm inner diameter) between the bioreactor and the hollow fibre module was designed to be as short as possible. Thus, the total length of the tubular baffle/dip tube (from the anchorage in the bottom of the bag to the connection to the ATF, P10 port) to the hollow fibre cartridge was 41 to 47 cm. The system was set up with compressed air and vacuum pump (Ilmvac). The pore size of the hollow fiber filters (GE Healthcare, Sweden) was 0.2 μm and the filter area was 850 $cm^2$.

FIG. 7 describes the general outline of the ATF-bioreactor setup. Alkali and addition bottles were connected by welding and could therefore be disconnected and refilled and rewelded again to the system. Two syringes, one 10 ml and one 50 ml, were used to do shots of glucose and glutamine.

TFF Setup

The bioreactor was connected to the hollow fibre cartridge (same specifications as above in the ATF section but as ReadyToProcess RTPCFP-2-E-4×2MS) by linking the P10 tubular baffle/dip tube (by ReadyMate™ connections) to the filter and the P9 tubular baffle/dip tube to the other end of the filter (FIGS. 5 and 9). The cell suspension was pumped from the bioreactor through the filter by a Watson Marlow 620S pump. The retained cells were then transported back to the bioreactor through port P9. Disposable pressure sensors (SciLog, USA) were also connected before and after the filter and on the permeate side (using ReadyMate™ connections).

Analytical Assays

Samples from the bioreactor and the harvest line were taken once or twice daily. Samples from the bioreactor (while rocking) was immediately analysed in the BioProfile Flex (Nova Biomedical, USA) that counted the number of live cells (viable cell density, given in million viable cells per mL (MVC/mL)) and the total number of cells (total cell density, given in million cells per mL) to monitor the cell growth, measured the average cell diameter. The concentration of glutamine, ammonia, glucose, lactate, pO2 and pCO2 in the sample was also measured in the Bioprofile Flex. Then the samples from the bioreactor were centrifuged at 3300 rpm for 5 minutes and the supernatants were aliquoted into Eppendorf tubes and put at −20° C. and −70° C. for the LDH analysis. Then the samples from the bioreactor were centrifuged at 3300 rpm for 5 minutes, aliquoted into Eppendorf tubes and kept at −20° C. The mAb concentration in the samples was analysed using Protein A HPLC method.

Example 1

ATF and TFF Perfusion

CHO Cell Growth

Figure 10:
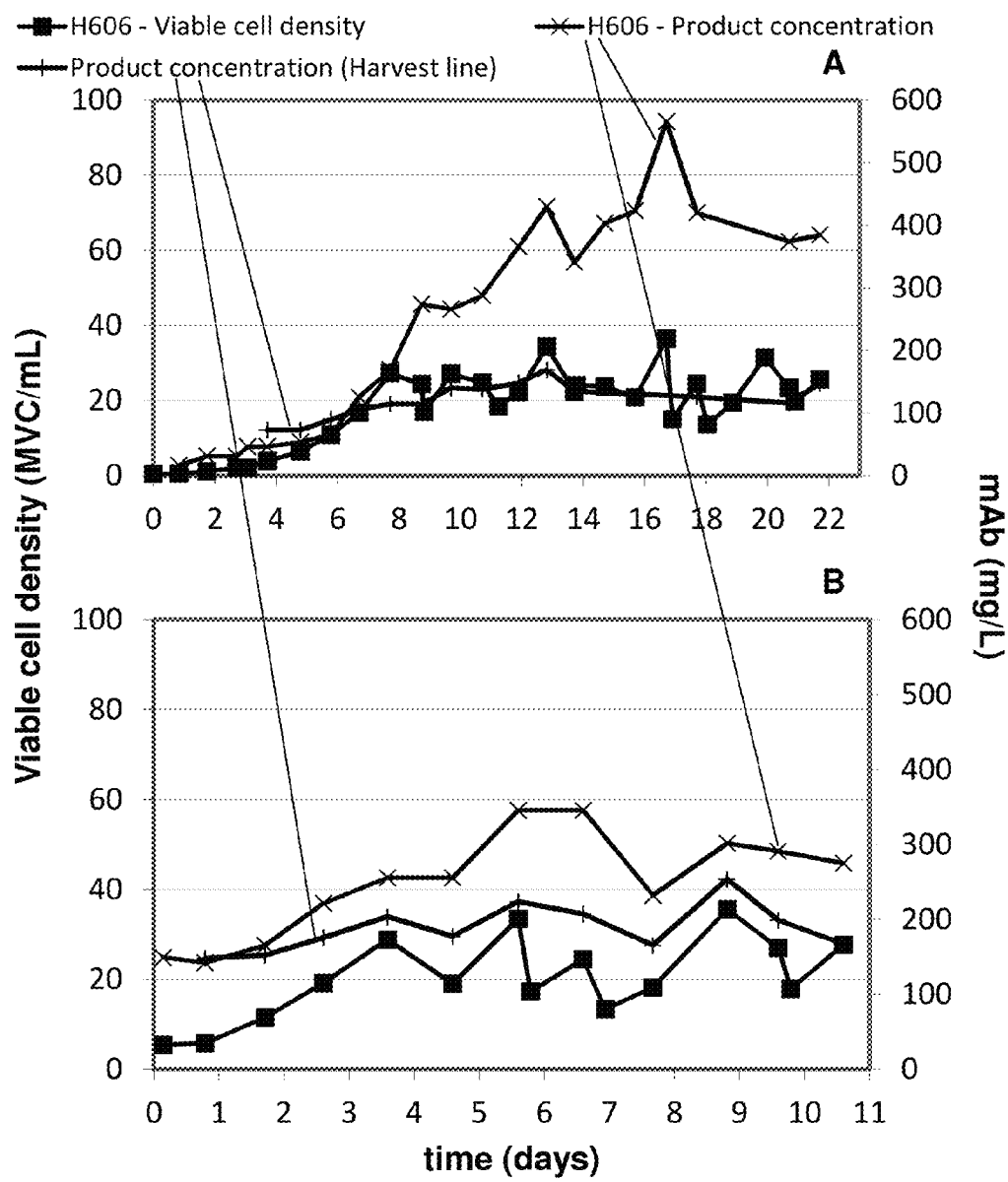
FIG. 10 shows the kinetics of recombinant IgG production by CHO cells cultivated according to the invention using the TFF system (A) and the ATF system (B).

CHO cells were cultivated in both systems of filtration, i.e. ATF or TFF system. FIG. 10 shows the cell density, viability and perfusion rate obtained during the TFF perfusion (FIG. 10A) and the ATF perfusion (FIG. 10B) cultivations. Two different types of culture media were used during the processes (HyClone PF-CHO Liquid Soy and IS CHO-CD XP). In order to minimize the shear stresses, the circulation flow rate in the external loop of the TFF system was set to 0.3 L/min, i.e. around 1000 s−1. This parameter also allowed a residence time of the cells outside of the reactor, i.e. at room temperature, lower than 1 min The average flow rate in the ATF system was 1 L/min during the entire process. For the TFF system, the bioreactor was inoculated at 0.4 MVC/mL in 4 L of IS CHO-CD XP medium, for the ATF system, the bioreactor was inoculated at 5 MVC/mL in Hyclone medium. A higher inoculation was chosen in order to reach a higher cell density rapidly and to subsequently be able to compare both cultures in parallel. Therefore, in an attempt to compare both processes, the IS medium used in the TFF system was changed into Hyclone medium after 11 days of culture. Using the IS medium, a comparison between both cultures was possible for few days; between days 3 and 6 and between days 11 and 18, for the ATF and TFF cultures respectively.

At the beginning of the process, cultivation using TFF system showed poor cell growth due to an inoculum taken from a batch culture in stationary phase. On the third day, when cell density reached around 2 MVC/mL, the perfusion was initiated and maintained around 1.2-1.5 L/d. The perfusion rate was decreased below 1 wv/day between days 5 and 6 and the perfusion was stopped for 8 hours on day 18 due to handling of culture medium. Hyclone medium was subsequently changed into a new IS CHO-CDXP medium on day 18.

After 8 days of cultivation, the first bleed was performed in order to maintain the cell density around 20 MVC/mL. Additional daily bleeds were performed during days 9-11, 13-15, 17-18, and 20-21. The bleed volume was taken into account when the daily perfusion rate was calculated.

For the ATF cultivation, perfusion was started directly after the inoculation of the bioreactor. As for the TFF system, the perfusion rate was kept around 1.5 wv/day and bleeds were considered when the rate was calculated. In addition, maintaining of the cell density around 20 MVC/mL was also achieved in this process by performing bleeds of the culture on days 4, 6, 7, 9 and 10.

Increase of the Agitation Rate

In both cultures, the DO control was performed by rocking speed. Previous experiments allowed to determine that agitation rate required (22-26 rpm, 7°) to maintain the DO close to the SP value (35%) when CHO cell concentration was kept around 20 MVC/mL. Enrichment of O2 in the inlet gas was used when necessary to further increase the amount of oxygen available for the cells (Table 3 and 4). The use of these parameters to reach the DO SP value and maintain a high viability (≥95%) was confirmed in both the ATF and TFF systems.

TABLE 3

Rocking rates and inclinations used during the ATF perfusion cultivation.

| Day(s) | Rocking rpm and angle | $O_2$ addition (%) |
| --- | --- | --- |
| 0-0.2 | 20 rpm @ 6° | 21 |
| 0.2-1.9 | 20-24 rpm @ 6° | 21 |
| 1.9-4.7 | 20-26 rpm @ 6° | 30-50 |
| 4.7-6.8 | 20-26 rpm @ 7° | 20-40 |
| 6.8-7 | 20-28 rpm @ 7° | 30 |
| 7-7.8 | 26 rpm @ 7° | 20-50 |
| 7.8-8.9 | 22-26 rpm @ 7° | 30-40 |
| 8.9-10.7 | 22-26 rpm @ 7° | 40 |

TABLE 4

Rocking rates and inclinations used during the TFF perfusion cultivation.

| Day(s) | Rocking rpm and angle | $O_2$ addition (%) |
| --- | --- | --- |
| 0-3 | 20 rpm @ 6° | 21 |
| 3-6.8 | 20-24 rpm @ 6° | 20-50 |
| 6.8-7.7 | 23-26 rpm @ 6° | 30-50 |
| 7.7-8 | 23 rpm @ 6° | 20-40 |
| 8-12.3 | 23-26 rpm @ 6° | 40-50 |
| 12.3-18 | 23-26 rpm @ 7° | 20-30 |
| 18-18.1 | 20-28 rpm @ 7° | 30 |
| 18.1-18.9 | 26 rpm @ 7° | 20-50 |
| 18.9-20 | 22-26 rpm @ 7° | 30-40 |
| 20-21.8 | 22-26 rpm @ 8° | 30-40 |

Cell Metabolism

For the TFF system, until day 11, the initial concentration of glucose in the IS medium was higher than the one in the Hyclone medium and IS medium used after the Hyclone medium (around 20 mM). The decrease of the initial concentration of glucose to 20 mM in these latter allowed to decrease the accumulation of lactate in the culture (20-25 mM vs. 35 mM). Under these conditions, the residual glucose concentration remained low, close to 3-5 mM, and shots of glucose performed daily were increased from 15 mM to 22 mM in both systems. Whereas in the TFF system, the residual glucose concentration was increased, in the ATF system, the increase of the shots of glucose was not sufficient to reach higher residual glucose concentration. The initial concentration of glutamine present in both culture media was around 4 mM. In both systems, although daily shots of glutamine to reach 2 mM were performed, glutamine was completely exhausted every day after the shots. The accumulation of ammonia was close to 4-5 mM, which is usually not considered as toxic. Therefore, to avoid a limitation of glutamine, it was decided to increase the target of glutamine from 2 mM to 4 mM during the 4 last days of the cultivations. As a result, residual glutamine concentration was maintained above at least 0.2 mM.

A maximal specific rate of recombinant IgG of 10-15 pg/cell/d was obtained, as well as a volumetric productivity close to 200 mg/L/d in both ATF and TFF systems.

Conclusions

The bag supported cell growth very well, in both ATF and TFF perfusion systems. Oxygen transfer was sufficient in the WAVE bioreactor and no limitation in the system set-up was detected. Different rocking/angle settings were used and different media were tested; the results showing the robustness of the system. Daily bleeds were used to avoid a too high cell density during this initial investigation phase.

Both the ATF and TFF systems appear to have equivalent performance concerning the cell growth and viability using either IS medium or Hyclone medium. For the TFF system, at high cell densities around 20-30 MVC/mL, a high viability ($\geq$95%) was maintained for 18 days.

Interestingly, the increase of rocking to 8° for the last days of the cultivation did not affect the viability, which was maintained as previously above 90%.

Example 2

High Density ATF and TFF Perfusion

CHO Cell Growth

Figure 11:
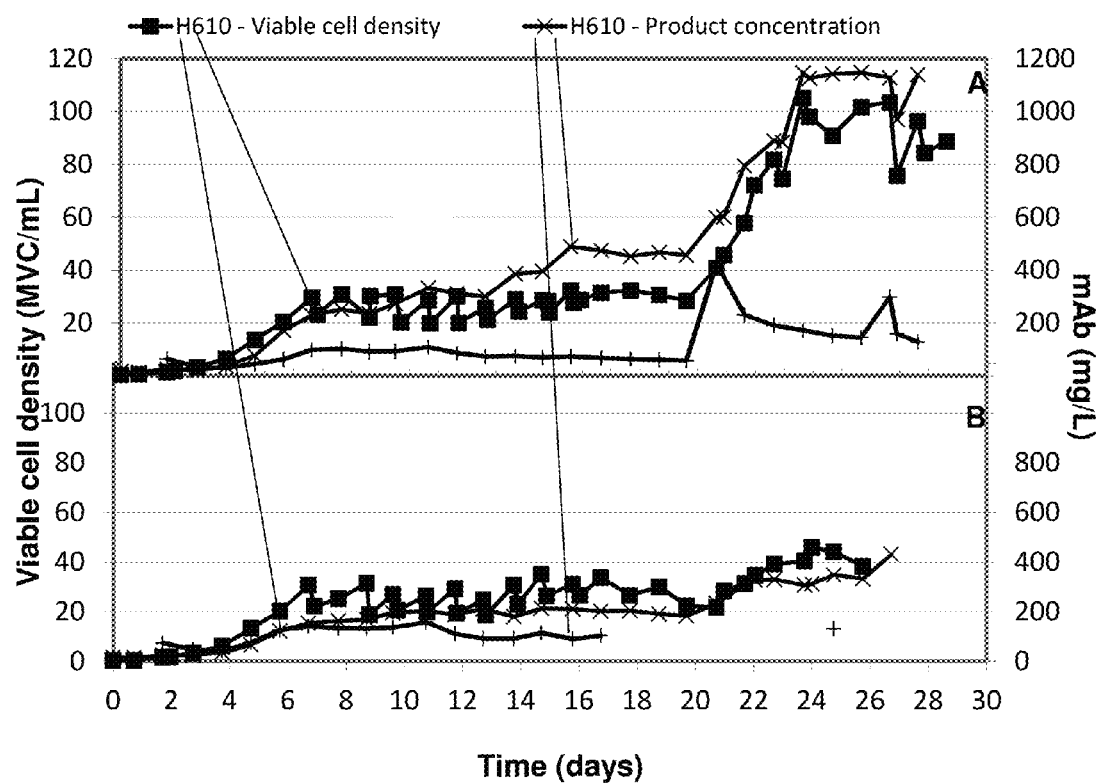
FIG. 11 shows the cell density, viability and perfusion rate in a 29-day perfusion process according to the invention using the TFF system (A) and in a 27-day perfusion process according to the invention using ATF system (B).
Figure 12:
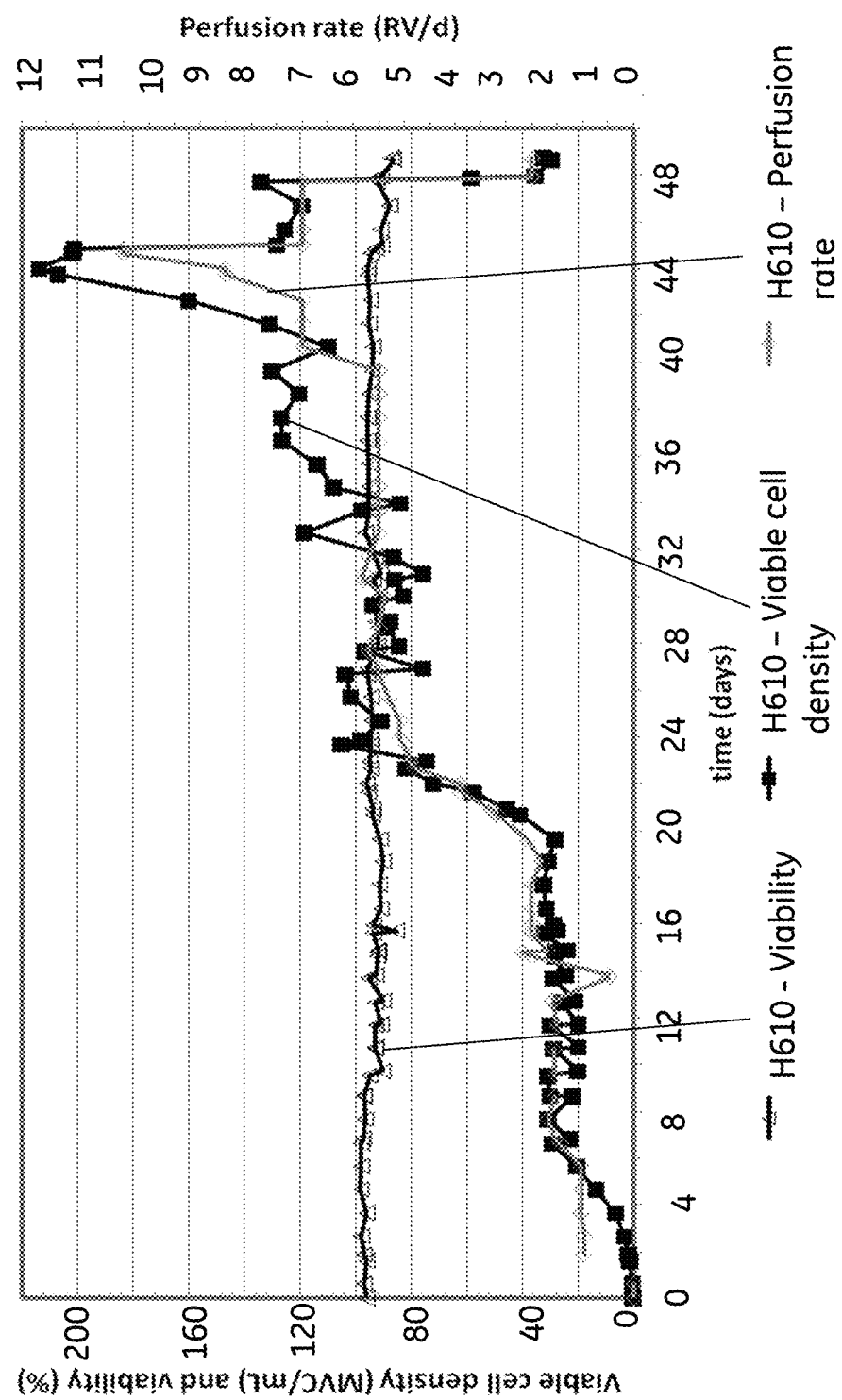
FIG. 12 shows the same data as FIG. 10A, when the TFF perfusion cultivation was continued for in total 49 days.

CHO cells were cultivated using IS medium in both systems, TFF and ATF, for 49 days and 27 days respectively (FIGS. 11 and 12). Whereas the cultivation using ATF system was stopped after 27 days of culture, the cultivation using TFF continued for 22 additional days. As for the previous cultivations, addition of anti-foam C was performed if needed, most generally every 3 or 7 days. In both processes, after 2 days of culture, a perfusion rate of 1 wv/d was applied until day 7. Similar results were again obtained regarding the CHO cell growth and the viability. Indeed, CHO cell concentration around 20-30 MVC/mL and a viability above 95% were observed. An agitation rate of 22-26 rpm with an angle of 7° allowed maintaining the DO close to the SP value and keeping a high viability ($\geq$95%). It was decided to increase the flow rate in the ATF system at the value used during previous cultivations, i.e. 1 L/min. In order to assess both filter devices during the same conditions, the flow rate in the external loop of the TFF was also increased to 1 L/min, which corresponds to a shear stress value of 3400 s−1. Furthermore, in an attempt to maintain a high viability in the ATF system, the perfusion rate was increased to 1.5 L/min.

Regarding the TFF system, the increase of the recirculation flow rate from 0.7 L/min to 1 L/min did not affect the CHO cell growth and the viability. Thus, the use of this flow rate enables to obtain high viability of the cells. The perfusion rate was progressively increased from 1.5 wv/d to 4 and 5 wv/d at the end of the culture for the ATF and TFF cultures respectively. During the 3 last days of the cultivation using ATF, although the perfusion rate was increased to 4 wv/d, the viability was not increased (close to 88-90%) and poor cell growth was observed. This result was correlated with an increase of the average cell diameter of the cells from 16.5-17.5 micron to 18-18.5 micron. Thus, since the status of the cells did not seem to be comparable any longer between both systems of filtration, it was decided to stop the ATF culture.

Surprisingly, in the TFF system, the increase of the perfusion rate to 5 wv/d resulted in very high cell densities, i.e. around 100 MVC/mL. Since day 23, bleeds had been performed daily in order to maintain these high cell densities between 80 and 105 MVC/mL. So, these high cell concentrations (around 100 MVC/mL) were maintained for one week with a high viability (between 92 and 95%). Following this, the cell density could be increased between 120 and 130 MVC/mL and maintained by daily bleeds for another week while maintaining a cell viability larger than 94%. In other words, the culture was kept stable at a cell density larger than 100 MVC/mL and cell viability larger than 94% for more than two weeks. The perfusion rate was then further increased up to 10 RV/day and surprisingly a cell density of more than 200 MVC/mL was observed with a maximum at 214 MVC/mL while the cell viability was larger than 94%. This extremely high cell density was kept for two days, and thereafter the perfusion rate was decreased again. In total, the TFF culture run for 49 days with the perfusion bag.

TABLE 5

Rocking rates, inclinations, O2 supply and airflow used during the ATF and TFF perfusion cultivation.

| Day | Rocking rate (rpm) | Rocking angle (degrees) | O2 supply (%) | Airflow (ppm) |
|---|---|---|---|---|
| 0-2 | 20 | 6 | 20 | 0.1 |
| 3 | 20 | 6 | 30 | 0.1 |
| 4 | 20 | 6 | 40 | 0.1 |
| 5 | 20-24 | 6 | 40 | 0.1 |
| 5 (1 h after) | 20-26 | 6 | 40 | 0.1 |
| 6 | 22-26 | 7 | 50 | 0.1 |
| 7 | 22-26 | 7 | 40 | 0.2 |
| 7 | 24-28 (step 1) | 7 | 30 | 0.2 |
| 7 (30 min after) | 24-28 (step 1) | 7 | 40 | 0.2 |
| 8 | 22-28 | 7 | 40 | |
| 8 (3 h after) | 22-26 | 7 | 50 | |
| 10 | 22-26 | 7 | 40 | 0.2 (TFF), 0.2-0.05 (ATF) |
| 10 (bubble effect study) | 22-28 (step 3) | 7 | 40 | 0.2 (TFF), 0.2-0.05 (ATF) |
| 11 | 22-26 | 7 | 40 | 0.2 (TFF), 0.2-0.05 (ATF) |
| 12 | 22-26 | 8 | 50 | 0.2 (TFF), 0.2-0.05 (ATF) |
| 13-18 | 22-26 | 7 | 50 | 0.2 (TFF), 0.2-0.05 (ATF) |

TABLE 5-continued

Rocking rates, inclinations, O2 supply and airflow used during the ATF and TFF perfusion cultivation.

| Day | Rocking rate (rpm) | Rocking angle (degrees) | O2 supply (%) | Airflow (ppm) |
|---|---|---|---|---|
| 19 | 26 (in ATF) | 6 | 50 | 0.2 |
| 20 | 22-26 | 8 (TFF), 7 (ATF) | 75 (TFF) | 0.2 |
| 21 | 24-26 (TFF), 22-26 (ATF) | 8 | 75 (TFF), 50 (ATF) | 0.2 |
| 22 | 24-26 (TFF), 22-26 (ATF) | 8 | 95 (TFF), 40 (ATF) | 0.2 |
| 23 | 24-26 (TFF), 22-26 (ATF) | 9 (TFF), 7 (ATF) | 100 (TFF), 40 (ATF) | 0.2 |
| 24 | 24-26 (TFF), 22-26 (ATF) | 9 (TFF), 7 (ATF) | 100 (TFF), 40 (ATF) | 0.2 |
| 25 | 24-26 (TFF), 22-26 (ATF) | 9 (TFF), 7 (ATF) | 95 (TFF), 44 (ATF) | 0.3-0.2 (TFF), 0.2 (ATF) |
| 26 | 24-26 (TFF), 22-26 (ATF) | 9 (TFF), 7 (ATF) | 100 (TFF), 44 (ATF) | |
| 27 | 24-26 (TFF), 22-26 (ATF) | 9 (TFF), 7 (ATF) | 100 (TFF), 44 (ATF) | 0.2 |
| 28 | 24-26 | 8 | 63-95 | 0.2 |
| 29 | 24-26 | 8 | 63-84 | 0.2 |
| 30 | 24-26 | 8 | 80-100 | 0.16-.3 |
| 31 | 24-26 | 8 | 78 | 0.27 |
| 32-36 | 24-26 | 8 | 80 | 0.3 |
| 37 | 24-26 | 8 | 80 | 0.41 |
| 38 | 24-26 | 8 | 80 | 0.43 |
| 39-42 | 24-26 | 8 | 80 | 0.36 |
| 43 | 24-26 | 8 | 95 | 0.36 |
| 44-45 | 24-28 | 8 | 100 | 0.58 |
| 46 | 25-27 | 8 | 88 | 0.33 |
| 47 | 25-28 | 8 | 100 | 0.5 |
| 48 | 24-26 26-27 | 7-8 | 30-50 | 0.2 |
| 49 | 24-26 | 7 | 50 | 0.2 |
| 50-52 | 24-26 | 8 | 100 | 0.2 |

Cell Metabolism

In both systems, the shots of glucose performed daily were increased when higher cell densities were reached in order to avoid a limitation of glucose. The accumulation of lactate did not exceed 35-40 mM; such concentrations are not considered toxic for the cells. The initial concentration of glutamine present in both culture media was around 4 mM. Although the shots of glutamine were increased, some limitations of glutamine occurred during the cultivations. During the last days of culture, the shots were really increased in order to avoid a limitation. The accumulation of ammonia was close to 4 mM in both cultures and even higher (around 7 mM) for the TFF culture when cell densities around 100 MVC/mL required an increase of glutamine addition.

IgG Production

A maximal specific rate of recombinant IgG of 10-15 pg/cell/d was obtained, as well as a volumetric productivity close to 200 mg/L/d. Similar results were obtained using the TFF system until day 20.

CONCLUSIONS

The bag of FIG. 5 with two sigmoidal tubular baffles/dip tubes has repeatedly been shown to support external perfusion in a WAVE bioreactor system by using ATF and TFF strategies for cell separation. Moreover, it has been shown to enable reaching extreme cell densities in the TFF system, without any foaming or filter clogging issues.

Two cultivation runs using ATF and two using TFF have been performed. During the four first runs (ATF and TFF), the cell density was maintained between 20 and 30 MVC/mL by daily cell bleeds. A perfusion rate of 1.5 wv/day was necessary in order to allow healthy cell growth at this cell density. Two commercial media from Irvine Scientific, IS, (used either with or without feed concentrate supplementation) and from Hyclone were used resulting in comparable cell growth and viability showing that the systems were robust for medium modifications.

Using the TFF system, cell densities of more than 100 MVC/were achieved at 5 wv/day. This cell density was kept during more than two weeks and maintained with daily cell bleed. Moreover, increasing the perfusion rate to 10 wv/day resulted in an extremely high cell density of >200 MVC/mL, up to 214 MVC/mL. This result was unexpected, and could not have been reached without the baffled bag. In this TFF system, one hollow fiber cartridge was used during four weeks without fouling. The long life time of the hollow fiber cartridge could potentially be attributed to the fact that the culture was constantly growing culture and had an excellent viability (≥94%) maintained during three weeks. An experiment using the ATF system was performed in parallel. Using this system a maximal cell density of 46 MVC/mL was achieved.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. It should be noted that elements and features from individual embodiments and/or aspects may be combined to create further embodiment.

The invention claimed is:

1. An inflatable bioreactor bag for cell cultivation comprising:
   a top sheet and a bottom sheet, each being formed of flexible material and joined together to form two end edges and two side edges;
   a plurality of tubular baffles, each tubular baffle being disposed within the inflatable bioreactor bag and mounted to the top sheet via a single inlet and outlet port corresponding to the tubular baffle for transporting material into and out of said inflatable bioreactor bag; and
   a plurality of diffusers mounted to the bottom sheet, each diffuser corresponding to each tubular baffle, and each diffuser is configured to mount each tubular baffle to the bottom sheet, wherein the tubular baffle extends in a direction away from the bottom sheet in a region where the shortest distance to the closest one of said two end edges is higher than about one fourth of the shortest distance between said two end edges, and wherein each diffuser comprising at least one opening forming an open flow-path for cell suspension through the diffuser and a lumen of the tubular baffle, wherein at least one baffle of the plurality of baffles is of a curved shape and in contact with the cell suspension within said inflatable bioreactor bag, and offset and spaced from the remaining of the plurality of the tubular baffles in the region.

2. The inflatable bioreactor bag of claim 1, wherein said inflatable bioreactor bag is equipped with sterile connectors and irradiated.

3. The inflatable bioreactor bag of claim 1, wherein each diffuser comprises a bottom ring or plate, a plurality of struts joining said bottom ring or plate to a tube connector and the opening is between said struts.

4. The inflatable bioreactor bag of claim 1, wherein at least one of the single inlet and outlet ports on said top sheet is further connected to at least one filter or a gravitational device, outside the inflatable bioreactor bag.

5. The inflatable bioreactor bag of claim 4, wherein said filter is a microfilter or an ultrafilter with a retentate side and a permeate side.

6. The inflatable bioreactor bag of claim 4, wherein said filter or gravitational device is further connected to an air actuated membrane pump.

7. The inflatable bioreactor bag of claim 5, wherein two of the single inlet and outlet ports on said top sheet are connected via a pump to the retentate side of said filter, forming a retentate loop.

8. A bioreactor comprising the inflatable bioreactor bag, the inflatable bioreactor bag comprising:
   a top sheet and a bottom sheet, each being formed of flexible material and joined together to form two end edges and two side edges;
   a plurality of tubular baffles, each tubular baffle being disposed within the inflatable bioreactor bag and mounted to the top sheet via a single inlet and outlet port corresponding to the tubular baffle for transporting material into and out of said inflatable bioreactor bag; and
   a plurality of diffusers mounted to the bottom sheet, each diffuser corresponding to each tubular baffle of the plurality of tubular baffles, and each diffuser is configured to mount each tubular baffle to the bottom sheet, wherein the tubular baffle extends in a direction away from the bottom sheet in a region where the shortest distance to any one of said two end edges is higher than about one fourth of the shortest distance between said two end edges, and wherein each diffuser comprising at least one opening forming an open flow-path for cell suspension through the diffuser and a lumen of the tubular baffle,
   wherein the inflatable bioreactor bag is mounted on a support which is pivotally mounted to a base about a movable axis generally parallel to said end edges,
   wherein at least one baffle of the plurality of baffles is of a curved shape and in contact with the cell suspension within said inflatable bioreactor bag, and configured to intensify agitation of the cell suspension, wherein the at least one baffle is offset and spaced from the remaining of the plurality of the tubular baffles in the region.

9. The inflatable bioreactor bag of claim 1, which is generally rectangular.

10. The inflatable bioreactor bag of claim 1, wherein said plurality of tubular baffles are prepared from an elastomeric material.

11. The inflatable bioreactor bag of claim 3, wherein said at least one opening of each diffuser have both length and width larger than 2 mm.

12. The inflatable bioreactor bag of claim 3, wherein said at least one opening of each diffuser have both length of 5-25 mm and width of 2.5-10 mm.

13. The inflatable bioreactor bag of claim 3, wherein each diffuser comprises a generally frustoconical cavity connected to said opening and to said tubular baffle.

14. The inflatable bioreactor bag of claim 4, wherein said filter is a hollow fiber cartridge.

* * * * *